United States Patent [19]

Cagnon et al.

[11] Patent Number: 4,592,874
[45] Date of Patent: * Jun. 3, 1986

[54] PROCESS FOR THE SYNTHESIS OF ALPHA-CHLORINATED CHLOROFORMATES

[75] Inventors: Guy C. Cagnon, Ballancourt; Marc D. Piteau, Itteville; Jean-Pierre G. Senet, La Chapelle, all of France; Roy A. Olofson; Jonathan T. Martz, both of State College, Pa.

[73] Assignee: Societe Nationale des Poudres et Explosifs, Paris, France

[ * ] Notice: The portion of the term of this patent subsequent to Jun. 3, 2003 has been disclaimed.

[21] Appl. No.: 260,907

[22] Filed: May 6, 1981

[30] Foreign Application Priority Data

May 14, 1980 [FR] France ................................. 80 10806

[51] Int. Cl.[4] ........................ C07C 68/02; C07C 69/96
[52] U.S. Cl. ..................................... 558/283; 558/281
[58] Field of Search ........................................ 260/463

[56] References Cited

U.S. PATENT DOCUMENTS

| 2,820,810 | 1/1958 | Frevel et al. ......................... 260/463 |
| 2,951,834 | 9/1960 | Scott .................................... 260/463 |
| 3,393,270 | 2/1976 | Ekstrom et al. ..................... 424/271 |
| 3,873,521 | 3/1975 | Ekström et al. .................. 260/239.1 |

FOREIGN PATENT DOCUMENTS

| 34536 | 8/1981 | European Pat. Off. . |
| 57422 | 8/1982 | European Pat. Off. . |
| 61162 | 9/1982 | European Pat. Off. . |
| 82404 | 6/1983 | European Pat. Off. . |
| 121223 | 6/1901 | Fed. Rep. of Germany . |
| 2628410 | 1/1978 | Fed. Rep. of Germany . |
| 2201870 | 5/1974 | France . |
| 2387988 | 11/1978 | France . |

OTHER PUBLICATIONS

Hennig, Chemical Abstracts, vol. 31, 2311[6] (1937).
Brysova, et al., Chemical Abstracts, vol. 84, 105502c (1976).
Olofson, et al., Chemical Abstracts, vol. 86, 71966f (1977).
Sugano, et al., Chemical Abstracts, vol. 90, 137829e, 137830y (1979).
Choi, Chemical Abstracts, vol. 92, 198390t (1980).
Mogyorodi, et al., Chemical Abstracts, vol. 95, 24530k (1981).
Macko, et al., Chemical Abstracts, vol. 53, 22706f (1959).
Czechoslovakian article, "Aliphaltic Esters of Carbamic Acid" by Macko and Gaher, Chem. Zvesti 13, pp. 436–445 (1959).
Beilstein, 4th Ed. vol. 3, pp. 12–13 (1921).
Matzner et al., "Chemical Reviews", vol. 64 pp. 645–656 (1964).
Müller; Lebig's Annalen der Chimie, vol. 257, p. 50 (1890).
Kirk-Othmer, "Encyclopedia of Chemical Technology, 3rd ed., vol. 5, John Wiley & Sons, New York, pp. 65–66.

Primary Examiner—Donald G. Daus
Assistant Examiner—Diana G. Rivers
Attorney, Agent, or Firm—Bucknam and Archer

[57] ABSTRACT

Process for the synthesis of α-chlorinated chloroformates, and new α-chlorinated chloroformates.

The invention relates to a new process for the manufacture of α-chlorinated chloroformates and, to new α-chlorinated chloroformates as new industrial products. The process according to the invention consists of a synthesis, by catalytic phosgenation, of α-chlorinated chloroformates of the formula:

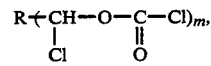

in which: R represents a substituted or unsubstituted hydrocarbon radical and m represents an integer superior or equal to one, this synthesis consisting in reacting phosgene with the aldehyde R$-$(CHO)$_m$, in the presence of a catalyst which is an organic or inorganic substance which is capable in a medium containing an aldehyde of the formula R$-$(CHO)$_m$, phosgene and, possibly, a solvent, of generating a pair of ions one of which is an halogenide anion and the other is a cation which is sufficiently separated from said halogenide anion so as to give to the latter a nucleophilic power enabling it to react with the function(s) aldehyde of the molecule R$-$(CHO)$_m$.

15 Claims, No Drawings

PROCESS FOR THE SYNTHESIS OF ALPHA-CHLORINATED CHLOROFORMATES

The invention relates to the manufacture of α-chlorinated chloroformates and to new α-chlorinated chloroformates as industrial products.

The synthesis of α-chlorinated chloroformates of the general formula:

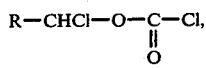

in which R is an aliphatic or aromatic substituent, is a very difficult undertaking if it is essential not to add a further chlorine atom to the radical R during the synthesis.

In Liebig's Annalen der Chemie of 1890, Volume 257, page 50 et seq., Müller proposed a process which is still the only one known and used at the present time. This process consists in photolytically chlorinating the corresponding chloroformate which is unsubstituted in the α-position. Unfortunately, numerous by-products which are more highly chlorinated than necessary are obtained in addition to the desired product. Thus, Müller counted no fewer than five by-products in the case of ethyl chloroformate which he studied.

Now, the presence of these by-products is extremely troublesome because of the main purpose for which the said chloroformates are applied, namely their conversion to carbonates which are especially useful in the synthesis of fine pharmaceutical products.

It is thus essential to distil the reaction product, although this is difficult because of the presence of numerous by-products.

There is another early publication, namely German Pat. No. 121,223 of 1901, which describes the synthesis of 1,2,2,2-tetrachloroethyl chloroformate and α-chlorobenzyl chloroformate by the phosgenation of chloral and benzaldehyde, respectively, in the presence of a stoichiometric amount of a tertiary amine which does not belong to the pyridine series.

If it is decided to attempt the phosgenation of aldehydes other than those above, for example acetaldehyde, under the same conditions, the formation of numerous complexes and byproducts is observed in addition to that of α-chloroethyl chloroformate, which is only obtained with a mediocre yield; this makes the process of no value on an industrial scale.

Furthermore, if it is also decided to attempt the phosgenation with an aliphatic tertiary amine, for example triethylamine, this amine is found to be essentially destroyed, only a very small amount of the derived chloroformate being formed.

There is therefore a need of a process for the manufacture of pure α-chlorinated chloroformates, if possible with a good yield, which will at last make it possible to guarantee these products, of very simple structure, the development which they deserve.

Applicants have now found such a process for the manufacture of α-chlorinated chloroformates free of by-products of subsequent substitution, which process uses inexpensive starting materials and leads to excellent yields. This process is the first of such general application to be proposed for 90 years.

The invention consists of a process for the synthesis of α-chlorinated chloroformates of the formula:

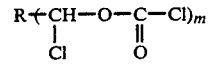

in which R represents a substituted or unsubstituted aliphatic, cycloaliphatic or aromatic hydrocarbon radical and m represents an integer greater or equal to one, characterised in that phosgene is reacted with the corresponding aldehyde, $R$-$(CHO)_m$, in the process of a catalyst.

According to the invention, phosgene is reacted with the aldehyde $R$-$(CHO)_m$ in the presence of a catalyst. This is indeed the basis of the invention because, since the beginning of the century, it has been thought that aldehydes were not capable of reacting with phosgene except in a few very particular cases where the reaction was carried out in the presence of stoichiometric amounts of basic organic substances, which were in fact assigned the role of a complexing agent of phosgene. It has been possible to find a definition which is common to a certain number of catalysts which are suitable within the scope of the invention. These catalysts are organic or inorganic substances which are capable in a medium containing an aldehyde of the formula $R$-$(CHO)_m$, phosgene and, possibly, a solvent of generating a pair of ions one of which is an halogenide anion and the other is a cation which is sufficiently separated from said halogenide anion so as to give to the latter a nucleophilic power enabling it to react with the function(s) aldehyde of the molecule $R$-$(CHO)_m$.

As catalysts according to the invention contemplated by this definition, the following substances, as such or under the form of their reaction product with phosgene, may notably be cited: tertiary amines, substituted amides, substituted ureas and thioureas, tertiary phosphines, substituted phosphoramides, onium halogenides such as halogenides of quaternary ammonium, phosphonium and arsonium, halogenides of tertiary sulfonium and metallic halogenides associated with a complexing agent of their cation. Preferably the halogenide is the chloride.

The invention also relates, by way of new industrial products, to the new α-chlorinated chloroformates which can be obtained by the process according to the invention and which are particularly useful as agents for synthesis.

The invention is thus remarkable in several respects: it makes it possible to phosgenate a large number of aldehydes and it demonstrates the possibility of carrying out this phosgenation in the presence of catalytic amounts of a very large variety of substances.

The process according to the invention, is not greatly influenced by the nature of the radical R.

This appears from experimental findings and also from considerations of chemical mechanisms since the aldehyde function is the principal function involved in the reaction and since R is not modified either in the final product or in any intermediate. On the contrary, features like the size of R may have an influence on certain operating conditions, although this is not surprising: for instance the presence of a of large molecular weight R leads to prefer a reaction temperature which is superior to the melting point of the aldehyde or to prefer the use of a solvent for the aldehyde.

The radical R can thus be a substituted or unsubstituted, saturated or unsaturated aliphatic or cycloaliphatic radical. It is thus possible, according to the invention, to phosgenate aldehydes as different as acetaldehyde, valeraldehyde, chloral, acrolein and cyclohexanecarboxaldehyde.

The radical R can also be a substituted or unsubstituted aromatic radical.

It is thus possible, according to the invention, to phosgenate benzaldehyde, 2-chlorobenzaldehyde and terephthalaldehyde. The process according to the invention can be applied to monoaldehydes as well as to polyaldehydes.

As has already been stated above, the process according to the invention consists of phosgenating the aldehyde corresponding to the desired α-chlorinated chloroformate, in the presence or in the absence of a solvent, in the presence of a catalyst. In the present description, the term "catalyst" is to be understood as having a restricted meaning. The compound added as a catalyst is essential for the reaction to proceed correctly, does not participate directly in the reaction and is used in relatively small amounts compared with the aldehyde; in this sense, it is indeed a catalyst; however, in contrast with what is commonly acknowledged in the case of catalysts, it cannot always be re-used for another reaction once the introduction of phosgene has been stopped, and applicants do not have any theoretical explanations of this phenomenon to put forward.

The proportion of catalyst employed is an important but not fundamental characteristic of the process according to the invention. In fact, in the case of a particularly efficient catalyst and a particularly reactive aldehyde, a proportion of 1 to 10 mol %, preferably 3 to 7%, of catalyst, relative to the molar amount of aldehyde groups to be converted, must be adopted. On the other hand, certain catalysts according to the invention are less efficient and a proportion of about 1 to 50%, preferably 5 to 40%, that is to say a higher average proportion, must be used. It can be said that, according to the invention, each catalyst has a maximum proportion beyond which it is found that the main reaction no longer takes place or is accompanied by significant secondary reactions. This maximum proportion is the lower, the greater the efficiency of the catalyst, and is the higher, the lower the activity of the catalyst. It has become apparent that, for the majority of catalysts, this maximum proportion is between about 10 and 50 mol %, relative to the molar amount of aldehyde groups to be converted. Thus, it is clear that it would still be within the scope of the present invention to adopt (1) as the catalyst, a compound which did not belong to one of the abovementioned families and which had a mediocre activity relative to good catalysts according to the invention (that is to say, for example, which represented only 10% or less of the activity of pyridine, all other things being equal), and (2) a proportion of the said catalyst of more than 50% or even a proportion which is equal to or greater than the stoichiometry of the reaction; in that case, in fact, the system would be economically much less satisfactory but, in contrast to that which is described in German Pat. No. 121,223, it would give rise mainly to the formation of the α-chlorinated chloroformate and would be applicable to the very large family of aldehydes mentioned above.

One of the most striking aspects of the present invention is the extremely wide variety of substances which can be employed as catalysts for the reaction. Applicants have tested a very large number of compounds and have been able to establish, on the one hand, a list of compounds which give good results, and, on the other hand, a test which enables those skilled in the art to determine whether a compound is a good catalyst in terms of the present invention.

As exposed hereinbefore certain catalysts are of the type which generates an halogenide anion, either directly or after reaction with phosgene.

In this case, the general mechanism by which the catalyst works is very probably as follows:

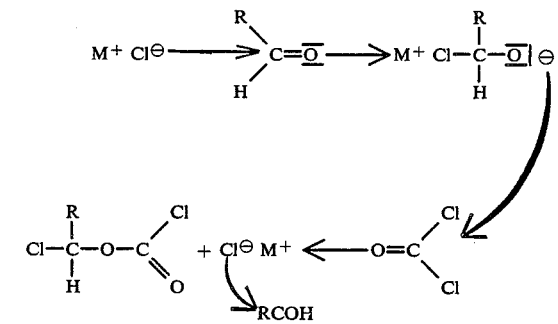

wherein $M^+$ represents an organic or inorganic cation, complexed or not, present as such in the catalyst from the beginning or formed at the beginning of the reaction by action of phosgene on the catalyst. Thus $M^+$ may be a complexed metal cation or an organic cation of the onium type and one has, then, for instance:

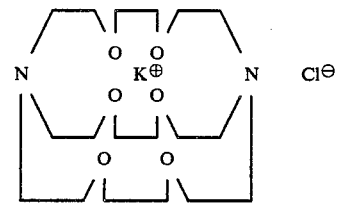

or $M^+$ issues from the more or less advanced reaction of phosgene on the substance responsible for the catalytic activity, like, for instance, in the following:

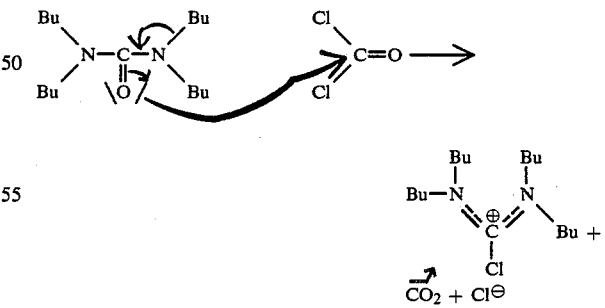

wherein $M^+$ is thus chlorimonium cation of high molecular weight.

It has been observed that the most valuable results are obtained with the following catalysts: aromatic tertiary amines containing a single aromatic nucleus, that is to say tertiary monoarylamines, such as N,N-dimethylaniline, N,N-dimethylaminopyridine and Michler's ketone or di-(para-dimethylaminophenyl)ketone, aromatic monoazines, such as pyridine, the non-aromatic cyclic amines employed in French Pat. No. 2,011,179 and especially imidazole, substituted amides and more particularly dimethylformamide, substituted ureas and thioureas and more particularly tetralkyl(thio)ureas, such as tetrabutylurea and tetramethylurea, tertiary phosphines and especially aliphatic tertiary phosphines, such as trioctylphosphine, and substituted phosphoramides and more particularly hexamethylphosphotriamide, quaternary ammonium, phosphonium and arsonium halogenides and tertiary sulfonium halogenides and, particularly those wherein all the substituting hydrocarbyl radicals comprise, taken altogether, at least 16 carbon atoms and, preferably, at least 4 carbon atoms each, such as tributyl benzyl ammonium chloride, metal halogenides associated with a complexing agent for their cation, such as the chlorides of alkali- and alkaline-earth metals, and particularly the potassium chloride, in association with a crown-ether such as 18-crown-6 or with a cryptand such as [222] or 1,10-diaza 4,7,13,16,21,24-hexaoxa(8,8,8)-bicyclo hexacosane. In the latter case, of course, the complexing agent which is associated is one which forms with the cation of the metal chloride a complex having a high stability constant: this is well known since a great deal of studies have been made such as the study by Kappenstein, Bulletin de la Société Chimique de France, 1974, Nos. 1-2, pages 89–109, and the study by J. M. Lehn, Structure and Bonding, Volume 16, pages 2–64, Springer Verlag, (1974). As regards aliphatic tertiary amines, they are catalysts of lower activity than the above compounds, within the scope of the present invention; in this respect, they are not preferred catalysts. It is understood by an halogenide, particularly a chloride, a bromide or a iodide, though it is clear that a chloride is preferred, so that even the first molecule of aldehyde, which is transformed due to the action of the halogenide anion coming from the catalyst, is transformed into the α-chloro chloroformate.

With the catalysts of the group comprising amides, ureas and tertiary phosphines, or with pyridine, phosgenation carried out at between 0° and 70° C. already gives good results; this is the case especially with catalysts like carboxamides, such as dimethylformamide, phosphoramides, such as hexamethylphosphotriamide, tetraalkyl-ureas or -thioureas, such as tetrabutylurea, tertiary phosphines, such as trioctyl phosphine, and of course pyridine. These catalysts will preferably be chosen if it is desired, for certain reasons, in particular the instability of the α-chlorinated chloroformate, to carry out the phosgenation at a moderate temperature. However, if the reaction is carried out at a temperature above 70° C., for example at about 100° C., an increase in the yield is generally observed with these same catalysts. Above 110° C., the risk of pyrolysis of the α-chlorinated chloroformate formed is incurred. On the other hand, the reaction generally proceeds satisfactorily with the most efficient catalysts down to −10° C., below which temperature the kinetics slow down fairly steeply.

With tertiary amines containing a single aromatic nucleus, such as N,N-dimethylaminopyridine or N,N-dimethylaniline, or also with imidazole, the phosgenation is preferably carried out above 70° C.

A test which enables those skilled in the art to say whether a compound is a catalyst in terms of the present invention consists of determining whether a yield of more than n% of α-chloroethyl chloroformate is obtained by reacting equimolecular amounts of acetaldehyde and phosgene, the reaction being carried out in a closed tube, in chlorobenzene, at 100° C., or in carbon tetrachloride at 40° C., whilst stirring, in the presence of n mol % of the said compound, relative to the acetaldehyde, the yield being measured relative to the starting acetaldehyde after 3 to 6 hours, and n being between 5 and 50 and preferably between 5 and 15.

It is not necessary to carry out this test on a very large scale. Thus, it suffices to introduce successively, at 0° C., 0,001 mol of the intended compound, a magnetised stirring bar and 5 ml of a solution containing 2 mols/liter of acetaldehyde and 5 ml of a solution containing 2 mols/liter of phosgene in chlorobenzene, into a 20 ml pressure-resistant glass tube, then to seal the said tube and to place it in a bath thermostatted at 100° C., the magnetic bar being used for constant stirring, and finally, after cooling to 0° C., to measure by nuclear magnetic resonance the yield of α-chloroethyl chloroformate obtained after 3 hours. In this case, the integration values a, b, c and d of the proton attached to the carbon in the α-position to the methyl groups of the following respective compounds are recorded: $CH_3CHO$, $CH_3CHClOCOCl$, $(CH_3CHO)_3$ (paraldehyde) and $CH_3CHCl_2$, after which it is seen whether the ratio $100\ b/a+b+c+d$ is greater than or equal to 5. If so, the compound tested is a catalyst according to the invention. By way of indication, it is recalled that quadruplets at 9.7, 6.45, 4.9 and 5.85 ppm correspond respectively to the abovementioned protons, the reference consisting of TMS.

According to the invention, the phosgenation is generally carried out under atmospheric pressure, but, in certain cases, it can be advantageous to carry out the reaction under a pressure which is above or below normal pressure; for example, in the case of the phosgenation of a volatile aldehyde, it can be useful to carry out the reaction under a pressure which is slightly above normal pressure.

The reaction may be carried out in a solvent which is inert towards phosgene or which ultimately leads, by reaction with the latter, to a solvent which is inert towards phosgene. This solvent is advantageously chosen, especially when the catalyst is not initially of the ionic type, from amongst non-polar or weakly polar and aprotic solvents, such as, for example, carbon tetrachloride, chloroform, methylene chloride, toluene, chlorobenzene and hexane.

Nevertheless, insofar as it is desired to phosgenate a very reactive aldehyde, such as, for example, acetaldehyde, a solvent which is slightly more polar than carbon tetrachloride is preferably chosen so as to avoid the risk of the formation of dichlorinated carbonate, and methylene chloride, for example, is thus preferred; in this case, it can also be advantageous to carry out the phosgenation at a relatively low temperature (35°–40° C.). Of course, it is also possible to carry out the reaction in a solvent medium consisting of the actual product which it is desired to form. Thus, it is possible to form a layer using α-chlorinated chloroformate originating from a previous manufacturing operation, and subsequently to introduce the reactants and catalyst. Another possibility consists of preparing a layer consisting of liquid phosgene and the catalyst, and subsequently introducing the aldehyde and the phosgene. According to a preferred embodiment, a layer is formed with liquid phosgene and the catalyst and, after reaction, the aldehyde and the remainder of phosgene are then introduced.

In this latter case, the reaction starts in the absence of solvent before subsequently proceeding in solution in the α-chlorinated chloroformate which is progressively formed.

It has been noticed that sometimes the polarity of the solvent has an effect on the yield in as much high as it has a high value. This is attributed to the fact that in a polar medium, the halogenide anion and the cation of the catalyst are better separated than in a weakly polar or apolar medium, so that a very high reactivity of the halogenide anion results.

The actual phosgenation reaction is carried out in accordance with the conventional techniques known to those skilled in the art. Thus, it is possible either to mix a solution of the phosgene in part of the solvent with a solution of aldehyde containing the catalyst, or also to bubble phosgene gas into a solution of aldehyde containing the catalyst. The actual phosgenation lasts several hours and is generally carried out in a stirred medium. After phosgenation, the α-chlorinated chloroformate is generally isolated from the reaction medium by conventional distillation under atmospheric or reduced pressure. Applicants have observed in this respect that, in the case of the synthesis of α-chlorinated chloroformates of the benzyl series, it is preferred to use pyridine as the catalyst with carbon tetrachloride as the solvent because, under these conditions, the catalyst or its reaction product with phosgene precipitates after phosgenation, and this makes it possible to isolate the α-chlorinated chloroformate by simple filtration, without distillation.

Taking account of the above, it is clear that the process according to the invention is not limited to a batch process. In fact, when the best catalysts are used, the reaction times are relatively short and the amounts of heat evolved by the reaction are modest; it is thus possible to carry out the reaction continuously and especially to use reactors arranged in a loop and fitted with ejectors or convergent/divergent nozzles, the reaction product being a good medium for carrying out the reaction, as stated above.

α-Chlorinated chloroformates are in great demand as agents for synthesis, in particular for the synthesis of fine pharmaceutical products. The invention also relates, by way of industrial products, to the new α-chlorinated chloroformates of the formula

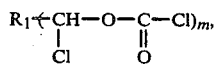

in which m represents an integer which can have a value greater or equal to one and $R_1$ represents: a substituted or unsubstituted saturated aliphatic radical containing at least two carbon atoms and at most 24 carbon atoms, a substituted or unsubstituted, monounsaturated or poly-unsaturated $C_2$-$C_{24}$ aliphatic radical, a substituted or unsubstituted $C_3$-$C_{24}$ cycloaliphatic radical or a substituted aromatic radical. The expression substituted radical is understood as meaning a radical carrying especially one or more halogen atoms or one or more groups which are inert towards phosgene or which give rise to inert groups by reaction with phosgene, such as $C_1$-$C_{12}$ alkyl groups, aryl, alkaryl or aralkyl groups or $NO_2$, NRR', CN, OR, OH, COOR, COR or OCOOR groups, in which R and R' are a hydrocarbon group.

The invention relates more particularly to the α-chlorinated chloroformates obtained from the following aldehydes: valeraldehyde, acrolein, 2-chlorobenzaldehyde, terephthalaldehyde and cyclohexanecarboxaldehyde.

It is in fact one of the advantages of the present invention that it makes it possible to obtain new α-chlorinated chloroformates which have not been described hitherto in the literature and which, in certain cases, cannot be obtained by the processes known hitherto, such as, in particular, the α-chlorinated chloroformates obtained from unsaturated aldehydes.

The examples given below illustrate the invention without limiting its scope.

EXAMPLE 1

44 g (1 mol) of freshly distilled acetaldehyde, 200 ml of anhydrous carbon tetrachloride and 120 g (1.2 mols) of phosgene are placed in a 500 ml reactor equipped with a stirrer, a thermometer, a solid carbon dioxide condenser and a dropping funnel. With the mixture kept at 0° C., 28.4 g (0.1 mol) of tetra-n-butylurea are added in the course of 15 minutes. The temperature is raised to 40° C. and the reaction is continued for 2 hours 30 minutes. After removal of the excess phosgene by degassing and of the solvent by evaporation, 72 g of 1-chloroethyl chloroformate, which distils at 117° C. (the literature indicates 115°-116° C.), are obtained, which corresponds to a yield of 50% by weight. As the formula of the product is:

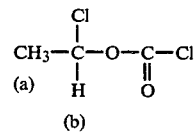

the infra-red spectrum shows a band at 1,780 cm$^{-1}$, corresponding to the C=O double bond, whilst the NMR spectrum, run in deuterated chloroform with tetramethylsilane as the reference, shows a doublet at 1.85 ppm, corresponding to the protons (a), and a quadruplet at 6.44 ppm, corresponding to the proton (b).

EXAMPLE 2

This example covers the synthesis of α-chloroethyl chloroformate from acetaldehyde, in the presence of hexamethylphosphotriamide. 1,000 ml of methylene chloride, washed with water and dried over magnesium sulphate, 440 g (10 mols) of anhydrous crude acetaldehyde and 179 g (1 mol) of hexamethylphosphorotriamide are introduced into a 3 liter glass reactor fitted with an anchor stirrer, a thermometer, a −35° C. condenser and a dip tube. The mixture is cooled to −5° C. and 1,107 g of phosgene gas are introduced in the course of 6 hours 30 minutes, whilst stirring.

The temperature of the reaction medium is then raised to 35°-40° C. and this temperature is maintained for 3 hours.

The mixture is left stand overnight at ambient temperature and the excess phosgene is then removed by sweeping with nitrogen for 2 hours 30 minutes.

The mixture obtained is then distilled under 150 mm Hg in a glass column (height: 40 cm, diameter: 3 cm, packed with 0.5 cm Fenske helices) and the fraction passing over at 68° C. is collected.

1,020.4 g of α-chloroethyl chloroformate are thus obtained, which corresponds to a yield of 71%, relative to the acetaldehyde used.

Analysis: infra-red spectrum (C=O): 1,780 cm$^{-1}$. $n_D^{20}$: 1.4220. density $d_{15}^{15}$: 1.2946.

EXAMPLE 3

This example covers the synthesis of α-chloroethyl chloroformate from acetaldehyde, in the presence of pyridine.

100 ml of methylene chloride, washed with water and dried over magnesium sulphate, 44 g (1 mol) of anhydrous crude acetaldehyde and 7.9 g (0.1 mol) of freshly distilled pyridine are introduced into a 500 ml glass reactor equipped with an anchor stirrer, a thermometer and an acetone/solid carbon dioxide reflux condenser. The mixture is cooled to between −5° and −10° C. and 120 g of phosgene are added in the course of about 1 hour.

The mixture is then heated under gentle reflux (temperature between 40° and 45° C.) for 3 hours 30 minutes.

The insoluble materials are filtered off under nitrogen and the filtrate is distilled under reduced pressure. 90 g (yield: 63%) of α-chloroethyl chloroformate (boiling point: 68° C./150 mm Hg) are thus obtained.

EXAMPLE 4

This example covers the synthesis of the α-chlorinated chloroformate obtained from valeraldehyde.

21.5 g (0.25 mol) of n-pentanal, 50 ml of carbon tetrachloride and 1.9 g (0.025 mol) of pyridine are introduced into a 100 ml reactor equipped as above. 30 g (0.3 mol) of phosgene are added to this mixture, cooled to −5° C., in the course of 30 minutes. The temperature is gradually raised to 40° C. After one hour at this temperature, the reaction mixture is degassed with nitrogen and filtered and the filtrate is distilled under reduced pressure. The α-chloro-n-pentyl chloroformate distils at 73° C. under 15 mm of mercury.

Weight obtained: 28 g, which corresponds to a yield of 60.5%.

Infra-red spectrum: C=O: 1,790 cm$^{-1}$.
$n_D^{20}$: 1.4377, density (20° C.): 1.1523.
NMR (CDCl$_3$, TMS):

$$CH_3CH_2CH_2CH_2\overset{Cl}{\underset{(d)}{\underset{|}{CH}}}O\overset{O}{\underset{\|}{C}}Cl$$
(a) (b) (c) (d)

(a) hump at 0.92 ppm (3H)
(b) hump at 1.40 ppm (4H)
(c) hump at 2.05 ppm (2H)
(d) triplet at 6.30 ppm (1H)

EXAMPLE 5

This example covers the synthesis of the α-chlorinated chloroformate obtained from acrolein.

The equipment and the procedure are identical to those of Example 4 and the following starting materials are used:

| | | |
|---|---|---|
| acrolein (propenal) | 28 g | (0.5 mol) |
| pyridine | 3.95 g | (0.05 mol) |
| carbon tetrachloride | 50 ml | |
| phosgene | 60 g | (0.6 mol) |

The α-chloroallyl chloroformate distils at 38° C. under 10 mm of mercury.

Weight obtained: 42 g, which corresponds to a yield of 54%

Infra-red spectrum: C=O: 1,780 cm$^{-1}$.
$n_D^{20}$: 1.4462, density (20° C.): 1.2853
NMR spectrum:

$$\underset{H(b)}{\overset{H(a)}{\diagdown}}C=C\underset{\underset{\underset{\|}{O}}{\overset{|}{OC-Cl}}}{\overset{H(c)}{\diagup}}\overset{Cl}{\diagdown}$$

(a) (b) (c): complex hump from 5.2 to 6.5 ppm (3H)
(d): doublet at 6.71 ppm (1H)

EXAMPLE 6

This example covers the synthesis of the α-chlorinated chloroformate obtained from benzaldehyde.

The products used are as follows:

| | | |
|---|---|---|
| benzaldehyde | 26.5 g | (0.25 mol) |
| pyridine | 1.95 g | (0.025 mol) |
| phosgene | 35 g | (0.35 mol) |
| carbon tetrachloride | 50 ml | |

Using a procedure identical to that of Example 4, 34.8 g (68%) of α-chlorobenzyl chloroformate, which distils at 70° C. under 0.4 mm of mercury, are obtained.

Infra-red spectrum: C=O: 1,770 cm$^{-1}$
$n_D^{20}$: 1.5367, density (20°): 1.3016
NMR spectrum:

all the protons have a chemical shift of between 7 and 8 ppm.

EXAMPLE 7

This example covers the synthesis of the α-chlorinated chloroformate obtained from 2-chlorobenzaldehyde.

Compared with Example 6, the benzaldehyde is replaced by 2-chlorobenzaldehyde.

25.1 g (yield: 42%) of α-chloro-2-chlorobenzyl chloroformate, which distils at 85°–88° C. under 0.2 mm Hg, are obtained.

Infra-red spectrum: C=O: 1,780 cm$^{-1}$.
$n_D^{20}$: 1.5420, density (20°C.): 1.4294.
NMR spectrum:

EXAMPLE 8

This example describes the synthesis of the α-chlorinated chloroformate obtained from terephthalaldehyde.

67 g (0.5 mol) of terephthalaldehyde, 3.95 g (0.05 mol) of pyridine and 100 ml of carbon tetrachloride are placed in a 500 ml reactor. 120 g (1.2 mols) of phosgene are then introduced at 0° C. The mixture is then heated gradually to 40° C. and kept at this temperature for 3 hours. After degassing, filtration and removal of the solvent, 133 g (yield: 80%) of a colourless oil are obtained.

Total chlorine content: calculated: 42.7, found: 40.02%

IR spectrum: C=O: 1,780 cm$^{-1}$.

NMR spectrum (CDCl$_3$, TMS):

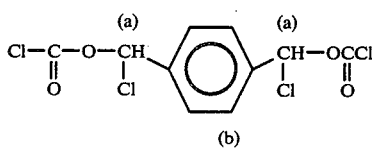

(a) singlet at 7.29 ppm (2H)
(b) singlet at 7.64 ppm (4H)

EXAMPLE 9

This example describes the synthesis of α-chloroethyl chloroformate from acetaldehyde, in the presence of trioctylphosphine.

11 g (0.25 mol) of acetaldehyde, 9.25 g (0.025 mol) of trioctylphosphine and 50 ml of carbon tetrachloride are placed in a 100 ml reactor. 30 g (0.3 mol) of phosgene are added to this mixture, cooled to 0° C. After heating at 35°-40° C. for 1 hour, the reaction mixture is degassed and distilled under reduced pressure (150 mm Hg). 9.1 g (yield: 25%) of α-chloroethyl chloroformate, which distils at 67°-68° C., are thus obtained.

EXAMPLE 10

This experiment describes the preparation of α-chloroethyl chloroformate by the phosgenation of acetaldehyde in the presence of 5 mol % of pyridine, in a solvent medium.

The procedure and the equipment are identical to those of Example 4.

The amounts of products used are as follows:

| | | |
|---|---|---|
| acetaldehyde | 11 g | (0.25 mol) |
| pyridine | 0.99 g | (0.0125 mol) |
| phosgene | 30 g | (0.3 mol) |
| methylene chloride | 50 ml | |

25.6 g (yield: 71.6%) of α-chloroethyl chloroformate, which distils at 68° C. under 150 mm of mercury, are thus obtained.

EXAMPLE 11

This experiment describes the preparation of α-chloroethyl chloroformate by the phosgenation of acetaldehyde in the presence of 5 mol % of pyridine, without a solvent.

22 g (0.5 mol) iof acetaldehyde and 1.98 g (0.025 mol) of pyridine are placed, at 0° C., in a 100 ml reactor equipped as in the preceding examples. 60 g (0.6 mol) of phosgene are introduced at this temperature. The reaction mixture is heated to 30° C. in the course of four hours and kept at this temperature for 1 hour. After removal of the phosgene, 42.1 g (yield: 59%) of α-chloroethyl chloroformate, which distils at 68° C. under 150 mm of mercury, are obtained.

EXAMPLE 12

This experiment describes the phosgenation of cyclohexanecarboxaldehyde.

28 g (0.25 mol) of cyclohexanecarboxaldehyde, 1.98 g (0.025 mol) of pyridine and 50 ml of carbon tetrachloride are placed in a 100 ml reactor. With this mixture cooled to 0° C., 30 g (0.3 mol) of phosgene are introduced. The reaction medium is then heated to 35°-40° C. and kept at this temperature for 1 hour.

After degassing, filtration and removal of the solvent under reduced pressure, 46 g (yield: 87%) of the expected chloroformate, which distils at 90°-93° C. under 10 mm of mercury, are obtained.

$n_D^{20}$: 1.4738, density (20° C.): 1.1934

NMR spectrum (CDCl$_3$, TMS):

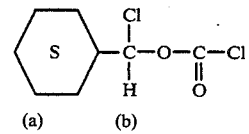

(a) hump from 1.15 to 2.2 ppm (11H)
(b) doublet at 6.1 ppm (1H)

EXAMPLES 13 TO 17

The purpose of these examples, which are carried out with the equipment of Example 4, is to illustrate the efficiency of various catalysts as a function of the temperature.

Each of these experiments was carried out on the following amounts:

| | | |
|---|---|---|
| acetaldehyde | 4.4 g | (0.1 mol) |
| toluene | 45 g | |
| catalyst | 0.01 mol | |
| phosgene | 12 g | (0.12 mol) |

The results obtained as a function of the temperature after a reaction time of 3 hours are shown in the table below, it being specified that the sign of a reaction or the absence of a reaction is assessed by infra-red spectrophotometry. The absence of a reaction indicates that the yield is below 5%.

| EXAMPLE No. | CATALYST | 40° C. | 70° C. | 100° C. |
|---|---|---|---|---|
| 13 | N,N—dimethylaminopyridine | no reaction | no reaction | reaction |
| 14 | N,N—dimethylaniline | no reaction | reaction | — |
| 15 | imidazole | no reaction | no reaction | reaction |
| 16 | reaction product of tetra n-butylurea with phosgene | reaction | — | — |

$$\begin{array}{c} C_4H_9 \\ \diagdown \\ C_4H_9 \diagup \end{array} N-C=N \begin{array}{c} Cl^- \; C_4H_9 \\ \diagup \\ \diagdown C_4H_9 \end{array}$$

| EXAMPLE No. | CATALYST | 40° C. | 70° C. | 100° C. |
|---|---|---|---|---|
| 17 | dimethylformamide | | reaction | |

EXAMPLES 18 TO 26

Two series of experiments were carried out on catalysts according to the invention in order to synthesise α-chloroethyl chloroformate.

These two series differ only by the reaction temperature and the solvent used.

0,001 mol of catalyst, a magnetised stirring bar and 5 ml of a solution containing 2 mols/liter of acetaldehyde and 5 ml of a solution containing 2 mols/liter of phosgene in carbon tetrachloride (series 1) or in chlorobenzene (series 2) were placed successively, at 0° C., in a 20 ml pressure-resistant sealable glass tube.

The amount of catalyst was thus 10 mol %, relative to the acetaldehyde.

The tube was then sealed rapidly and placed in a bath thermostatted at 40° C. (series 1) or at 100° C. (series 2).

The stirring effected by the magnetised bar was started and the reaction was left to proceed for 3 hours. After this period, the tube was cooled to about 0° C. and a sample of the reaction medium was taken and immediately analysed by NMR (reference: TMS). Since the reaction is carried out in a closed vessel, there is no loss of acetaldehyde, which is found again in one of the following 4 forms:

$CH_3CH_aO$: a quadruplet at 9.7 ppm corresponds to $H_a$ and has the integration value a.

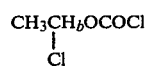

a quadruplet at 6.45 ppm corresponds to $H_b$ and has the integration value b.

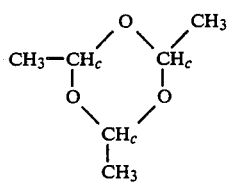

a quadruplet at 4.9 ppm corresponds to $H_c$ and has the integration value c.

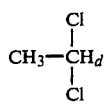

a quadruplet at 5.85 ppm corresponds to $H_d$ and has the integration value d.

The yields of α-chloroethyl chloroformate obtained with each of the catalysts were determined using the formula:

| | 100b / (a + b + c + d) | | | | |
|---|---|---|---|---|---|
| | Catalysts | | | | |
| Yield, Series | TBU (a) | Pyridine | TMU (b) | Quinoline | MK (c) |
| Yield in % Series 1 (CCl₄, 40° C.) | 45 | 100 | 45 | 10 | 15 |
| Yield in % Series 2 (chlorobenzene, 100° C.) | 75 | — | 75 | 65 | 65 |

(a) tetrabutylurea
(b) tetramethylurea
(c) Mischler's Ketone

EXAMPLE 27

In a keller reactor of 50 ml equipped with a magnetic stirrer and a acetone-Dry-Ice ® condenser maintained at −50° C., were introduced 1.30 g (0.0175 mole) of KCl, 0,040 g (0.00106 mole) of Kryptofix [222] commercialized by Merck, 12.5 g (0.125 Mole) of phosgene and, finally, 2.2 g (0.05 mole) of acetaldehyde.

The reaction mixture was then stirred for 5 hours at room temperature (18°-22° C.). At the end of this period the analysis of the medium by NMR shows that the yield of α-chloroethyl chloroformate is 96%, the residue being practically solely constituted by acetaldehyde.

A list of complexing agents, and particularly of cryptands, which may be used as the preceding Kriptofix [222], though, possibly, in association with a more convenient salt such as NaCl, can be found in the issue 1/77 of a review published by the Merck Company, Kontabte, pages 11–31. It will be particularly noticed that the association of NaCl with the polymer Kryptofix [222 B] constitutes an insoluble catalyst which can work in the absence of a solvent.

EXAMPLE 28

Tetra-n-hexyl ammonium bromide (0.5 g), phosgene (6.25 g) and acetaldehyde (1.1 g) were introduced in this order in a Claisen reactor of 50 ml. This mixture was allowed to stand under stirring during 4 hours at room temperature (18°-20° C.). After this period of time, the NMR spectrum of the mixture shows that it contains only α-chloro ethyl chloroformate. The yield was thus 100%, which is remarkable.

I claim:

1. The process for the synthesis of α-chlorinated chloroformates of the formula

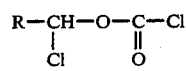

wherein: R is alkyl of 1 to 4 carbon atoms or R is =CCl₃ which consists of reacting phosgene with an aldehyde of formula RCHO, wherein R has the same meaning as above in the presence of a catalyst which is a member selected from the group consisting of (a) quaternary ammonium, phosphonium or arsonium halogenide, wherein the hydrocarbyl radicals attached to the N, P or As atom comprise together at least 16 carbon atoms, and (b) metal halogenides associated with a crown ether or a cryptand.

2. The process according to claim 1 wherein the metal halogenide is an alkali or an alkaline earth metal halogenide.

3. The process according to claim 1 wherein the reaction is carried out at between −10° and 110° C.

4. The process according to claim 1 wherein the aldehyde is reacted with phosgene in the presence of a solvent which is inert to phosgene or which ultimately leads by reaction with phosgene to a solvent which is inert towards phosgene.

5. The process according to claim 1 wherein the catalyst is used in an amount of 3–7 mole percent with respect to the molar amount of aldehyde.

6. The process according to claim 3 wherein the reaction is carried out at 0°–70° C.

7. The process according to claim 4 wherein the reaction is carried out in a non-polar or weakly polar aprotic solvent which is inert towards phosgene.

8. The process according to claim 5 wherein the solvent is the reaction product itself.

9. The reaction according to claim 4 which is carried out in a polar solvent.

10. The process according to claim 1 which is carried out continuously.

11. The process according to claim 2 wherein the catalyst is 1,10-diaza 4,7,13,16,21,24-hexaoxa(8,8,8)-bicyclo hexacosane, associated with KCl or with NaCl.

12. The process according to claim 1 wherein the catalyst is tetra-n-hexyl ammonium bromide or tri-n-butyl benzyl ammonium chloride.

13. The process according to claim 1 wherein the halogenide is a chloride or bromide.

14. The process according to claim 1 wherein the catalyst is a quaternary ammonium halogenide and each of said hydrocarbyl radicals contains at least four carbon atoms.

15. The process according to claim 1, wherein the aldehyde is acetaldehyde, chloral or valeraldehyde.

* * * * *